United States Patent [19]

Samuelsson et al.

[11] 3,954,835
[45] May 4, 1976

[54] 4,5-CIS-DIDEHYDRO-PGF$_1$ COMPOUNDS

[75] Inventors: Bengt Samuelsson, Stockholm, Sweden; Barney J. Magerlein, Portage, Mich.

[73] Assignee: The Upjohn Company, Kalamazoo, Mich.

[22] Filed: Feb. 7, 1974

[21] Appl. No.: 440,628

Related U.S. Application Data

[63] Continuation of Ser. No. 248,005, April 27, 1972, abandoned.

[52] U.S. Cl. ............... 260/468 D; 260/240 R; 260/211 R; 260/242; 260/268 R; 260/293.6 S; 260/326.2; 260/345.2; 260/410; 260/429.9; 260/439 R; 260/448 R; 260/448.8 R; 260/488 R; 260/501.1; 260/501.15; 260/501.17; 260/501.2; 260/514 D; 424/305; 424/317
[51] Int. Cl.$^2$ .................. C07C 69/74; C07C 61/30
[58] Field of Search ........ 260/408 D, 514 D, 488 R, 260/410

[56] References Cited
UNITED STATES PATENTS
3,711,515  1/1973  Kelly .............................. 260/343.3

OTHER PUBLICATIONS
March Advanced Organic Chemistry, pp. 662–663, (1968).
Fieser et al., Organic Reagents, p. 671 (1967).
Van Dorp, N. Y. Acad. of Sci., 180, pp. 184–186 (1970).

*Primary Examiner*—Robert Gerstl
*Attorney, Agent, or Firm*—Morris L. Nielsen

[57] ABSTRACT

This invention is a group of 4,5-didehydro and 4,5,17,18-tetradehydro PG$_1$ (prostaglandin-type) compounds, and processes for making them. These compounds are useful for a variety of pharmacological purposes, including anti-ulcer, inhibition of platelet aggregation, increase of nasal patency, labor inducement at term, and wound healing.

12 Claims, No Drawings

4,5-CIS-DIDEHYDRO-PGF₁ COMPOUNDS

This is a continuation of application Ser. No. 248,005, filed Apr. 27, 1972.

BACKGROUND OF THE INVENTION

This invention relates to novel compositions of matter, to novel methods for producing those, and to novel chemical intermediates useful in those processes. Particularly, this invention relates to certain novel analogs of some of the known prostaglandins in which a cis carbon-carbon double bond links C-4 and C-5 in the carboxy-terminated chain.

The known prostaglandins include, for example, prostaglandin $E_2$ ($PGE_2$), prostaglandin $F_2$ alpha and beta ($PGF_{2\alpha}$ and $PGF_{2\beta}$), prostaglandin $A_2$ ($PGA_2$), prostaglandin $B_2$ ($PGB_2$), and the corresponding PGE compounds. Each of the above-mentioned known prostaglandins is a derivative of prostanoic acid which has the following structure and atom numbering:

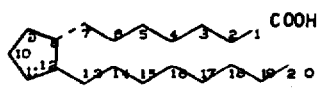

See, for example, Bergstrom et al., Pharmacol. Rev. 20, 1 (1968), and references cited therein. A systematic name for prostanoic acid is 7-[(2β-octyl)-cyclopent-1α-yl]heptanoic acid.

$PGE_2$ has the following structure:

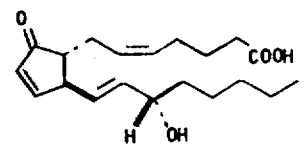

$PGF_{2\alpha}$ has the following structure:

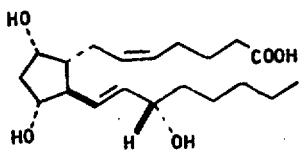

$PGF_{2\beta}$ has the following structure:

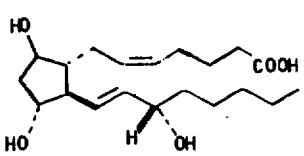

$PGA_2$ has the following structure:

$PGB_2$ has the following structure:

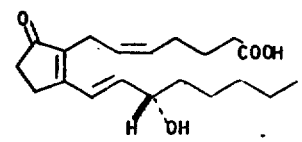

Each of the known $PG_3$ prostaglandins, $PGE_3$, $PGF_{3\alpha}$, $PGF_{3\beta}$, $PGA_3$, and $PGB_3$, has a structure the same as that shown for the corresponding $PG_2$ compound except that, in each, C-17 and C-18 are linked with a cis carbon-carbon double bond. For example, $PGE_3$ has the following structure:

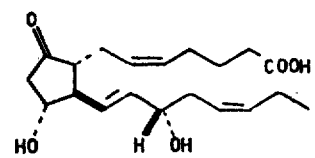

In formulas II to VII, as well as in the formulas given hereinafter, broken line attachments to the cyclopentane ring indicate substituents in alpha configuration i.e., below the plane of the cyclopentane ring. Heavy solid line attachments to the cyclopentane ring indicate substituents in beta configuration, i.e., above the plane of the cyclopentane ring.

The side-chain hydroxy at C-15 in formulas II to VII is in S configuration. See Nature, 212, 38 (1966) for discussion of the stereochemistry of the prostaglandins.

Molecules of the known prostaglandins each have several centers of asymmetry, and can exist in racemic (optically inactive) form and in either of the two enantiomeric (optically active) forms, i.e., the dextrorotatory and levorotatory forms. As drawn, formulas II to VII each represent the particular optically active form of the prostaglandin which is obtained from certain mammalian tissues, for example, sheep vesicular glands, swine lung, or human seminal plasma, or by carbonyl and/or double bond reduction of that prostaglandin. See, for example, Bergstrom et al., cited above. The mirror image of each of formulas II to VII represents the other enantiomer of that prostaglandin. The racemic form of a prostaglandin contains equal numbers of both enantiomeric molecules, and one of formulas II to VII and the mirror image of that formula is needed to represent correctly the corresponding racemic prostaglandin. For convenience hereinafter, use of the terms $PGE_1$, $PGE_2$, $PGF_{2\alpha}$, and $PGF_{3\alpha}$, will mean the optically active form of that prostaglandin with the same absolute configuration as $PGE_1$ obtained from mammalian tissues. When reference to the racemic form of one of those prostaglandins is intended, the word "racemic" or "dl" will preceed the prostaglandin name, thus, racemic $PGE_2$ or dl-$PGF_{2\alpha}$.

$PGE_2$, $PGE_3$, and the corresponding $PGF_\alpha$, $PGF_\beta$, PGA, and PGB compounds, and their esters, acylates, and pharmacologically acceptable salts, are extremely potent in causing various biological responses. For that reason, these compounds are useful for pharmacological purposes. See, for example, Bergstrom et al., cited above. A few of those biological responses are systemic arterial blood pressure lowering the case of the PGE, $PGF_\beta$, and PGA compounds as measured, for example, in anesthetized (pentobarbital sodium) pentolinium-treated rats with indwelling aortic and right heart cannulas; pressor activity, similarly measured, for the $PGF\alpha$ compounds; stimulation of smooth muscle as shown, for example, by tests on strips of guinea pig ileum, rabbit duodenum, or gerbil colon; potentiation of other smooth muscle stimulants; antilipolytic activity as shown by antagonism of epinephrine-induced mobilization of free fatty acids or inhibition of the spontaneous release of glycerol from isolated rat fat pads; inhibition of gastric secretion in the case of the PGE and PGA compounds as shown in dogs with secretion stimulated by food or histamine infusion; activity on the central nervous system; controlling spasm and facilitating breathing in asthmatic conditions; decrease of blood platelet adhesiveness as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen; and in the case of the PGE and PGB compounds, stimulation of epidermal proliferation and keratinization as shown when applied in culture to embryonic chick and rat skin segments.

Because of these biological responses, these known prostaglandins are useful to study, prevent, control, or alleviate a wide variety of diseases and undesirable physiological conditions in birds and mammals, including humans, useful domestic animals, pets, and zoological specimens, and in laboratory animals, for example, mice, rats, rabbits, and monkeys.

For example, these compounds, and especially the PGE compounds, are useful in mammals, including man, as nasal decongestants. For this purpose, the compounds are used in a dose range of about 10 $\mu$g. to about 10 mg. per ml. of a pharmacologically suitable liquid vehicle or as an aerosol spray, both for topical application.

The PGE, $PGF_\alpha$, and PGA compounds are useful in the treatment of asthma. For example, these compounds are useful as bronchodilators or as inhibitors of mediators, such as SRS-A, and histamine which are released from cells activated by an antigen-antibody complex. Thus, these compounds control spasm and facilitate breathing in conditions such as bronchial asthma, bronchitis, bronchiectasis, pneumonia and emphysema. For these purposes, these compounds are administered in a variety of dosage forms, e.g., orally in the form of tablets, capsules, or liquids; rectally in the form of suppositories; parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day, the exact dose depending on the age, weight, and condition of the patient and on the frequency and route of administration. For the above use these prostaglandins can be combined advantageously with other anti-asthmatic agents, such as sympathomimetics (isoproterenol, phenylephrine, ephedrine, etc); xanthine derivatives (theophylline and aminophyllin); and corticosteroids (ACTH and prednisolone). Regarding use of these compounds see South African Patent No. 68/1055.

The PGE and PGA compounds are useful in mammals, including man and certain useful animals, e.g., dogs and pigs, to reduce and control excessive gastric secretion, thereby reducing or avoiding gastrointestinal ulcer formation, and accelerating the healing of such ulcers already present in the gastrointestinal tract. For this purpose, the compounds are injected or infused intravenously, subcutaneously, or intramuscularly in an infusion dose range about 0.1 $\mu$g. to about 500 $\mu$g. per kg. of body weight per minute, or in a total daily dose by injection or infusion in the range about 0.1 to about 20 mg. per kg. of body weight per day, the exact dose depending on the age, weight, and condition of the patient or animal, and on the frequency and route of administration.

The PGE, $PGF_\alpha$, and $PGF_\beta$ compounds are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response, especially in emergency situation, the intravenous route of administration is preferred. Doses in the range about 0.005 to about 20 mg. per kg. of body weight per day are used, the exact dose depending on the age, weight, and condition of the patient or animal, and on the frequency and route of administration.

The PGE, $PGF_\alpha$, and $PGF_\beta$ compounds are especially useful as additives to blood, blood products, blood substitutes, and other fluids which are used in artifical extracorporeal circulation and perfusion of isolated body portions, e.g., limbs and organs, whether attached to the original body, detached and being preserved or prepared for transplant, or attached to the new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of those at a total steady state dose of about 0.001 to 10 mg. per liter of circulating fluid. It is especially useful to use these compounds in laboratory animals, e.g., cats, dogs, rabbits, monkeys, and rats, for these purposes in order to develop new methods and techniques for organ and limb transplants.

PGE compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore, $PGE_2$, for example, is useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the PGE compound is administered by intravenous infusion immediately after abortion or delivery at a dose in the range about 0.01 to about 50 μg. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight, and condition of the patient or animal.

The PGE, PGA, and PGF$_\beta$ compounds are useful as hypotensive agents to reduce blood pressure in mammals, including man. For this purpose, the compounds are administered by intravenous infusion at the rate about 0.01 to about 50 μg. per kg. of body weight per minute, or in single or multiple doses of about 25 to 500 μg. per kg. of body weight total per day.

The PGA compounds and derivatives and salts thereof increase the flow of blood in the mammalian kidney, thereby increasing volume and electrolyte content of the urine. For that reason, PGA compounds are useful in managing cases of renal disfunction, especially in cases of severely impaired renal blood flow, for example, the hepatorenal syndrome and early kidney transplant rejection. In cases of excessive or inappropriate ADH (antidiuretic hormone; vasopressin) secretion, the diuretic effect of these compounds is even greater. In anephretic states, the vasopressin action of these compounds is especially useful. Illustratively, the PGA compounds are useful to alleviate and correct cases of edema resulting, for example, from massive surface burns, and in the management of shock. For these purposes, the PGA compounds are preferably first administered by intravenous injection at a dose in the range 10 to 1000 μg. per kg. of body weight or by intravenous infusion at a dose in the range 0.1 to 20 μg. per kg. of body weight per minute until the desired effect is obtained. Subsequent doses are given by intravenous, intramuscular, or subcutaneous injection or infusion in the range 0.05 to 2 mg. per kg. of body weight per day.

The PGE, PGF$_\alpha$, and PGF$_\beta$ compounds are useful in place of oxytocin to induce labor in pregnant female animals, including man, cows, sheep, and pigs, at or near term, or in pregnant animals with intrauterine death of the fetus from about 20 weeks to term. For this purpose, the compound is infused intravenously at a dose of 0.01 to 50 μg. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started. An alternative route of administration is oral.

The PGE, PGF$_\alpha$, and PGF$_\beta$ compounds are useful for controlling the reproductive cycle in ovulating female mammals, including humans and animals such as monkeys, rats, rabbits, dogs, cattle, and the like. By the term ovulating female mammals is meant animals which are mature enough to ovulate but not so old that regular ovulation has ceased. For that purpose, $PGF_{2\alpha}$, for example, is administered systemically at a dose level in the range 0.01 mg. to about 20 mg. per kg. of body weight of the female mammal, advantageously during a span of time starting approximately at the time of ovulation and ending approximately at the time of menses or just prior to menses. Intravaginal and intrauterine are alternative routes of administration. Additionally, expulsion of an embryo or a fetus is accomplished by similar administration of the compound during the first third of the normal mammalian gestation period.

As mentioned above, the PGE compounds are potent antagonists of epinephrine-induced mobilization of free fatty acids. For this reason, this compound is useful in experimental medicine for both in vitro and in vivo studies in mammals, including man, rabbits, and rats, intended to lead to the understanding, prevention, symptom alleviation, and cure of diseases involving abnormal lipid mobilization and high free fatty acid levels, e.g., diabetes mellitus, vascular diseases, and hyperthyroidism.

The PGE and PGB compounds promote and accelerate the growth of epidermal cells and keratin in animals, including humans, useful domestic animals, pets, zoological specimens, and laboratory animals. For that reason, these compounds are useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For these purposes, these compounds are preferably administered topically at or near the site where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns or skin loss due to other causes, systemic administration is advantageous, for example, by intravenous injection or infusion, separate or in combination with the usual infusions of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. To illustrate, a wet dressing for topical application to second and/or third degree burns of skin area 5 to 25 square centimeters would advantageously involve use of an isotonic aqueous solution containing 1 to 500 μg./ml. of the PGB compound or several times that concentration of the PGE compound. Especially for topical use, these prostaglandins are useful in combination with antibiotics, for example, gentamycin, neomycin, polymyxin B, bacitracin, spectinomycin, and oxytetracycline, with other antibacterials, for example, mafenide hydrochloride, sulfadiazine, furazolium chloride, and nitrofurazone, and with corticoid steroids, for example, hydrocortisone, prednisolone, methylprednisolone, and fluprednisolone, each of those being used in the combination at the usual concentration suitable for its use alone 4,5-Didehydro-PGE$_1$ is mentioned in the prior art (see van Dorp, Annals N.Y. Acad. Sci. vol. 180, page 181, esp. pp. 184–185, 1971).

SUMMARY OF THE INVENTION

It is a purpose of this invention to provide novel prostaglandin analogs in which a cis carbon-carbon double bond links C-4 and C-5 in the carboxy-terminated chain. It is a further purpose to provide esters, lower alkanoates, and pharmacologically acceptable salts of said analogs. It is a further purpose to provide a novel process for preparing said acids and esters. It is still a further purpose to provide novel intermediates useful in said process.

The presently described acids and esters of the 4,5-unsaturated prostaglandin analogs include compounds of the following formulas, and also the racemic compounds of each respective formula and the mirror image thereof:

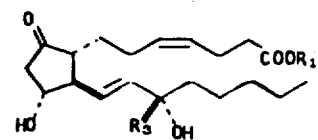 VIII

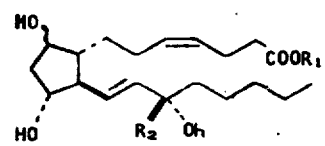 IX

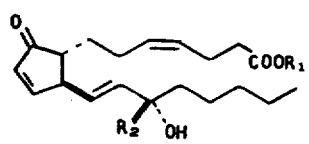 X

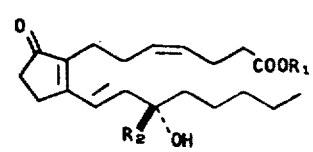 XI

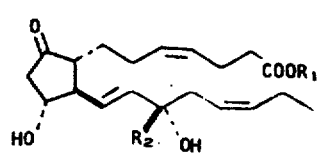 XII

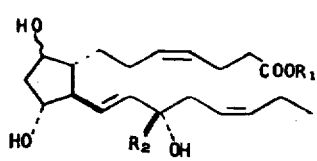 XIII

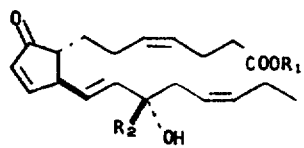 XIV

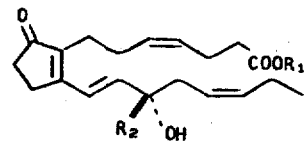 XV

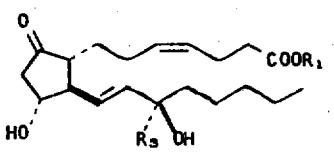 XVI

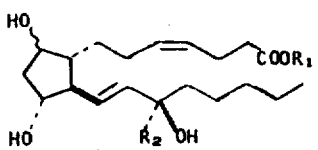 XVII

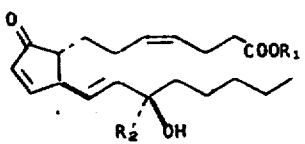 XVIII

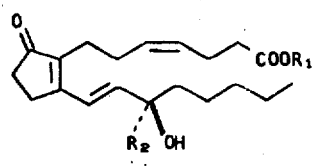 XIX

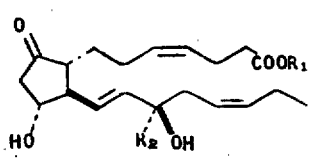 XX

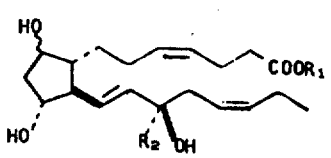 XXI

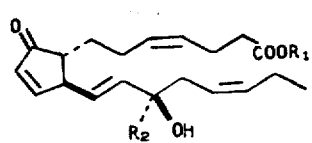 XXII

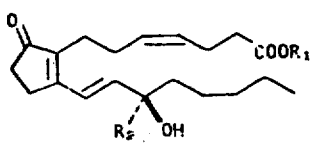

XXIII

In Formulas VIII to XXIII, $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one to 3 chloro or alkyl of one to 4 carbon atoms, inclusive; $R_2$ is hydrogen, methyl, or ethyl; $R_3$ is methyl or ethyl; and the wavy line ~ indicates attachment to the cyclopentane ring in alpha or beta configuration.

Formula IX represents 4,5-cis-didehydro-$PGF_{1\alpha}$ when $R_1$ and $R_2$ are hydrogen and ~ indicates the alpha configuration. Formula XII represents 4,5-cis-17,18-cis-tetradehydro-$PGE_1$ when $R_1$ and $R_2$ are hydrogen. Formula XVII represents 4,5-cis-didehydro-15$\beta$-$PGF_{1\beta}$, methyl ester, when $R_1$ is methyl, $R_2$ is hydrogen, and ~ indicates the beta configuration.

As in the case of formulas II to VII, formulas VIII to XV are each intended to represent optically active prostanoic acid derivatives with the same absolute configuration as $PGE_1$ obtained from mammalian tissues. Furthermore, formulas VIII to XV represent compounds having the S configuration at C-15, i.e. wherein the hydroxyl is attached to the side chain in alpha configuration. Also included within this invention are the 15-epimer compounds corresponding to

of formulas XVI to XXIII wherein the C-15 hydroxyl is in $\beta$ (beta) configuration. Hereinafter, "15$\beta$" refers to the epimeric configuration. Thus, "4,5-cis-didehydro-15$\beta$-$PGF_{1\alpha}$," identifies a compound of formula XVII, similar to that of formula IX except that it has the beta (or R) configuration at C-15 instead of the natural alpha (or S) configuration of 4,5-cis-didehydro-$PGF_1$. Each of formulas VIII to XV plus its mirror image describe a racemic compound within the scope of this invention; likewise each of the 15-epimer formulas corresponding to formulas XVI to XXIII plus its mirror image describe a racemic compound within the scope of this invention. For convenience hereinafter, such a racemic compound is designated by the prefix "racemic" (or "dl") before its name; when that prefix is absent, the intent is to designate an optically active compound represented by the appropriate formula VIII to XXIII.

With regard to formulas VIII to XXIII, examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof. Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 2-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl. Examples of aralkyl of 7 to 12 carbon atoms, inclusive, are benzyl, phenethyl, 1-phenylethyl, 2-phenylpropyl, 4-phenylbutyl, 3-phenybutyl, 2-(1-naphthylethyl), and 1-(2-naphthylmethyl). Examples of phenyl substituted by one to 3 chloro or alkyl of one to 4 carbon atoms, inclusive, are p-chlorophenyl, m-chlorophenyl, o-chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, 4-chloro-2-methylphenyl, and 2,4-dichloro-3-methylphenyl.

Accordingly, there is provided an optically active compound of the formula

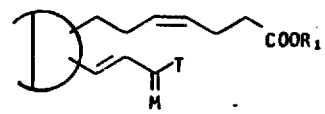

XXIV or a racemic compound of that formula and the mirror image thereof, wherein $\mathcal{D}$ is one of the three carbocyclic moieties:

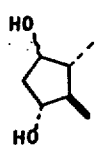 , 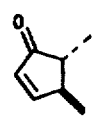 , or  , wherein ~ indicates attachment of hydroxyl to the cyclopentane ring in alpha or beta configuration; wherein M is

or

wherein $R_2$ is hydrogen, methyl, or ethyl; wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive; and wherein T is 1-pentyl or cis 1-pent-2-enyl; including the lower alkanoates thereof, and the pharmacologically acceptable salts thereof when $R_1$ is hydrogen.

Formula XXIV, which is written in generic form for convenience represents PGF $\alpha$ -type compounds when $\mathcal{D}$ is

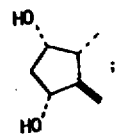

PGF$_\beta$ -type compounds when D is

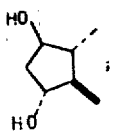

PGA-type compounds when D is

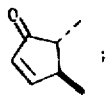

and PGB-type compounds when D is

There is also provided an optically active compound of the formula

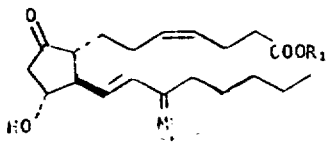

or a racemic compound of that formula and the mirror image thereof, wherein M' is

or

wherein R$_3$ is methyl or ethyl; wherein R$_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive; including the lower alkanoates thereof, and the pharmacologically acceptable salts thereof when R$_1$ is hydrogen.

There is further provided an optically active compound of the formula

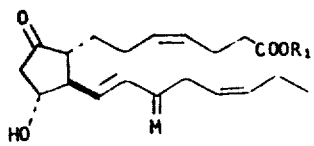

XXVI or a racemic compound of that formula and the mirror image thereof, wherein M is

or

wherein R$_2$ is hydrogen, methyl or ethyl; and wherein R$_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive; including the lower alkanoates thereof, and the pharmacologically acceptable salts thereof when R$_1$ is hydrogen.

The novel formula VIII-to-XXIII compounds and the racemic compounds of this invention each cause the biological reponses described above for the PGE, PGF$_\alpha$, PGF$_\beta$, PGA, and PGB compounds, respectively, and each of these novel compounds is accordingly useful for the above-described corresponding purposes, and is used for those purposes in the same manner as decribed above.

The known PGE, PGF$_\alpha$, PGF$_\beta$, PGA, and PGB compounds are all potent in causing multiple biological responses even at low doses. For example, PGE$_1$ and PGE$_2$ both cause vasodepression and smooth muscle stimulation at the same time they exert antilipolytic activity. Moreover, for many applications, these known prostaglandins have an inconveniently short duration of biological activity. In strking contrast, the novel prostaglandin analogs of formulas VIII to XXIII and their racemic compounds, are substantially more specific with regard to potency in causing prostaglandin-like biological responses, and have a substantially longer duration of biological activity. Therefore, each of these novel prostaglandin analogs is surprisingly and unexpectedly more useful than one of the corresponding above-mentioned known prostaglandins for at least one of the pharmacological purposes indicated above for the latter, because it has a different and narrower spectrum of biological potency than the known prostaglandin, and therefore is more specific in its activity and causes smaller and fewer undesired side effects than when the known prostaglandin is used for the same purpose. Moreover, because of its prolonged activity, fewer and smaller doses of the novel prostaglandin analog can frequently be used to attain the desired result.

Another advantage of the novel compounds of this invention, especially the preferred compounds defined hereinabove, compared with the known prostaglandins, is that these novel compounds are administered effectively orally, sublingually, intravaginally, buccally, or rectally, in addition to usual intravenous, intramuscular, or subcutaneous injection or infusion methods indicated above for the uses of the known prostaglandins. These qualities are advantageous because they facilitate maintaining uniform levels of these compounds in the body with fewer, shorter, or smaller doses, and make possible self-administration by the patient.

The 4,5-didehydro and 4,5,17,18-tetradehydro PGE$_1$, PGF$_{1\alpha}$, PGF$_{1\beta}$, PGA$_1$, and PGB$_1$ type compounds encompassed by Formulas VIII to XXIII including their alkanoates, are used for the purposes described above in the free acid form, in ester form, or in pharmacologically acceptable salt form. When the ester form is used, the ester is any of those within the above definition of $R_1$. However, it is preferred that the ester be alkyl of one to 12 carbon atoms, inclusive. Of those alkyl, methyl and ethyl are especially preferred for optimum absorption of the compound by the body or experimental animal system; and straight-chain octyl, nonyl, decyl, undecyl and dodecyl are especially preferred for prolonged activity in the body or experimental animal.

Pharmacologically acceptable salts of these Formula VIII-to-XXIII compounds useful for the purposes described above are those with pharmacologically acceptable metal cations, ammonium, amine cations, or quaternary ammonium cations.

Especially preferred metal cations are those derived from the alkali metals, e.g., lithium, sodium and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about 18 carbons atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)-diethanolamine, galactamine, N-methylglucamine, N-methylglucosamine, ephedrine, phenylephrine, epinephrine, procaine, and the like.

Examples of suitable pharmacologically acceptable quanternary ammonium cations are tetramethylammonium, tetraethylammonium, benzyltrimethylammonium, phenyltriethylammonium, and the like.

The compounds encompassed by Formulas VIII to XXIII are used for the purposes described above in free hydroxy form or also in the form wherein the hydroxy moieties are transformed to lower alkanoate moieties, e.g., —OH to —OCOCH$_3$. Examples of lower alkanoate moieties are acetoxy, propionyloxy, butyryloxy, valeryloxy, hexanoyloxy, heptanoyloxy, octanoyloxy, and branched chain alkanoyloxy isomers of those moieties. Especially preferred among these alkanoates for the above described purposes are the acetoxy compounds. These free hydroxy and alkanoyloxy compounds are used as free acids, as esters, and in salt form all as described above.

As discussed above, the compounds of Formulas VIII to XXIII are administered in various ways for various purposes; e.g., intravenously, intramuscularly, subcutaneously, orally, intravaginally, rectally, bucally, sublingually, topically, and in the form of sterile implants for prolonged action. For intravenous injection or infusion, sterile aqueous isotonic solutions are preferred. For that purpose, it is preferred because of increased water solubility that $R_1$ in the Formula VIII-to-XXIII compound be hydrogen or a pharmacologically acceptable cation. For subcutaneous or intramuscular injection, sterile solutions or suspensions of the acid, salt, or ester form in aqueous or non-aqueous media are used. Tablets, capsules, and liquid preparations such as syrups, elixirs, and simple solutions with the usual pharmaceutical carriers are used for oral sublingual administration. For rectal or vaginal administration, suppositories prepared as known in the art are used. For tissue implants, a sterile tablet or silicone rubber capsule or other object containing or impregnated with the substance is used.

The 4,5-didehydro and 4,5,17,18-tetradehydro PGE$_1$-, PGF$_{1\alpha}$ -, PGF$_{1\beta}$ -, PGA$_1$-, and PGB$_1$-type compounds encompassed by formulas VIII to XXIII are produced by the reactions and procedures described and exemplified hereinafter.

Reference to Chart A, herein will make clear the transformation from the formula-XXVII lactol compounds to the formula-XXX PGF-type compounds by steps 1–3, inclusive. Formulas XXVII, XXVIII, XXIX, and XXX, hereinafter referred to, are depicted in Chart A, wherein $R_4$ is alkyl of one to 4 carbon atoms, inclusive, THP is tetrahydropyranyl, T is 1-pentyl or cis 1-pent-2-enyl, and ~ indicates attachment of OH or OTHP in alpha or beta configuration. Examples of alkyl of one to 4 carbon atoms, inclusive, are methyl, ethyl, propyl, isopropyl, butyl, isobutyl, sec-butyl, and

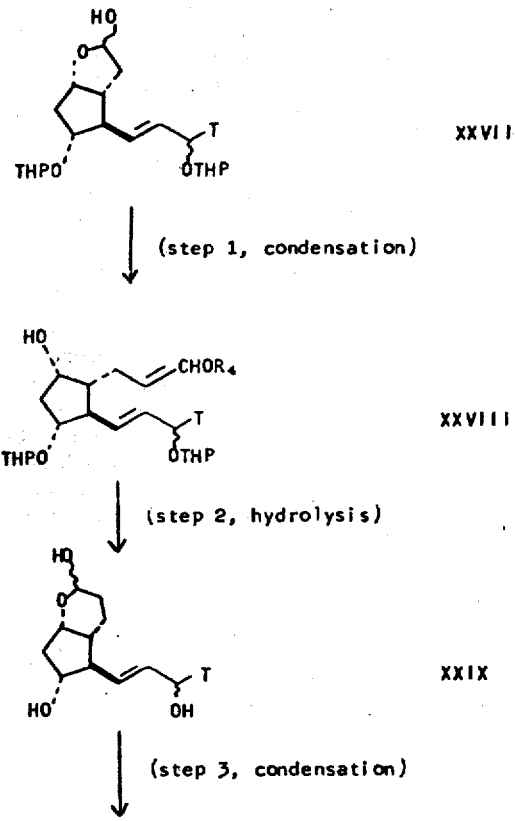

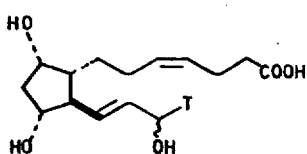

XXX tert-butyl.

Consider, first, step 1 of Chart A wherein the formula-XXVII compounds undergo condensation to form the formula-XXVIII enol ethers. For this purpose, an alkoxymethylenetriphenylphosphorane is useful. See, for example, Levine, J. Am. Chem. Soc. 80, 6150 (1958). The reagent is conveniently prepared from a corresponding quaternary phosphonium halide and a base, e.g. butyl lithium or phenyl lithium, at a low temperature, e.g. preferably below −10° C. The formula-XXVII lactol is mixed with the reagent and the condensation proceeds smoothly within the temperature range −30° C. to +30° C. At higher temperatures the reagent is unstable, whereas at low temperatures the rate of condensation is undesirably slow. Examples of the alkoxy-methylenetriphenylphosphoranes preferred for forming the formula-XXVIII enol ethers are methoxy-, ethoxy-, propoxy-, isopropoxy-, butoxy-, isobutoxy-, sec-butoxy-, and tertbutoxymethylenetriphenylphosphorane.

Various hydrocarbyloxymethylenetriphenylphosphoranes which may be substituted for the alkoxymethylenetriphenylphosphoranes and are therefore useful for preparing formula-XXVIII intermediates wherein $R_4$ is hydrocarbyl, include alkoxy (of 4 to 18 carbon atoms)-, aralkoxy-, cycloalkoxy-, and aryloxymethylenetriphenylphosphoranes. Examples of these hydrocarbyloxymethylenetriphenylphosphoranes are 2-methylbutoxy-, isopentyloxy-, heptyloxy-, octyloxy-, nonyloxy-, tridecyloxy-, octadecyloxy-, benzyloxy-, phenethyloxy-, p-methylphenethyloxy-, 1-methyl-3-phenylpropoxy-, cyclohexyloxy-, phenoxy-, and p-methylphenoxymethylenetriphenylphosphorane. See, for example, Organic Reactions, Vol. 14, pages 346–348, John Wiley and Sons, Inc., N.Y., (1965).

Consider, next, step 2 of Chart A, wherein the formula-XXVIII enol ether intermediates are hydrolyzed to the formula-XXIX lactols. This hydrolysis is done under acidic conditions, for example with perchloric acid or acetic acid. Tetrahydrofuran is a suitable diluent for this reaction mixture. Reactions temperatures of from 10° C. to 100° C. may be employed. The length of time required for hydrolysis is determined in part by the hydrolysis temperature. With acetic acid-water-tetrahydrofuran at about 60° C., several hours are sufficient.

Finally in step 3 of Chart A, the formula-XXIX lactols are transformed to the formula-XXX PGF-type products by condensation with a Wittig reagent derived from 3-carboxypropyltriphenylphosphonium halide and sodio methylsulfinylcarbanide. Dimethyl sulfoxide is conveniently used as a solvent, and the reaction may be done at about 25° C.

The various formula-XXVIII and -XXIX intermediates are useful directly as produced or they may be subjected to separation procedures, for example silica gel chromatography or recrystallization.

The initial optically active and racemic reactants of formula XXVII in Chart A and their 15β-epimers are known in the art or are prepared by methods known in the art. See, for example, Corey et al., J. Am. Chem. Soc. 92,397 (1970) and 93, 1490 (1971). Use of the lactol wherein T is 1-pentyl yields a 4,5-cis-didehydro-$PGF_{1\alpha}$ product; use of the lactol wherein T is cis 1-pent-2-enyl yields a 4,5-cis-17,18-cistetradehydro-$PGF_{1\alpha}$ product. The stereochemistry at C-15 is preserved, i.e. a 15β formula-XXVII reactant yields a 15β formula-XXX product.

Reference to Chart B, herein, will make clear the transformation from the PCF-type compounds XXXI to the PGE-type compounds XXXIV by steps 1–3, inclusive. Formulas XXXI, XXXII, XXXIII, and XXXIV, hereinafter referred to, are depicted in Chart B, wherein A is alkyl of one to 4 carbon atoms, inclusive, phenyl, phenyl, substituted with one or 2 fluoro, chloro, or alkyl of one to 4 carbon atoms, inclusive, or aralkyl of 7 to 12 carbon atoms, inclusive; wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive; wherein R is $R_1$ as defined above or silyl of the formula —Si-$(A)_3$ wherein A is as defined above; wherein T is 1-pentyl or cis 1-pent-2-enyl; and wherein ~ indicates attachment of hydroxyl or silyl in alpha or beta configuration. The various A's of a —Si-$(A)_3$ moiety are alike or different. For example, an —Si-$(A)_3$ can be trimethysilyl, dimethylpropylsilyl, dimethylphenylsilyl, or methylphenylbenzylsilyl. Examples of alkyl of one to 4 carbon atoms, inclusive, are methyl, ethyl, propyl, isopropyl, butyl, isobutyl, sec-butyl, and tert-butyl. Examples of aralkyl of 7 to 12 carbon atoms, inclusive, are benzyl, phenethyl, α-phenylethyl, 3-phenylpropyl, α-naphthylmethyl, and 2-(β-naphthyl)ethyl, Examples of phenyl substituted with one or 2 fluoro, chloro, or alkyl of one to 4 carbon atoms, inclusive, are p-chlorophenyl, m-fluorophenyl, o-tolyl, 2,4-dichlorophenyl, p-tertbutyl, 4-chloro-2-methylphenyl, and 2,4-dichloro-3-methylphenyl.

CHART B

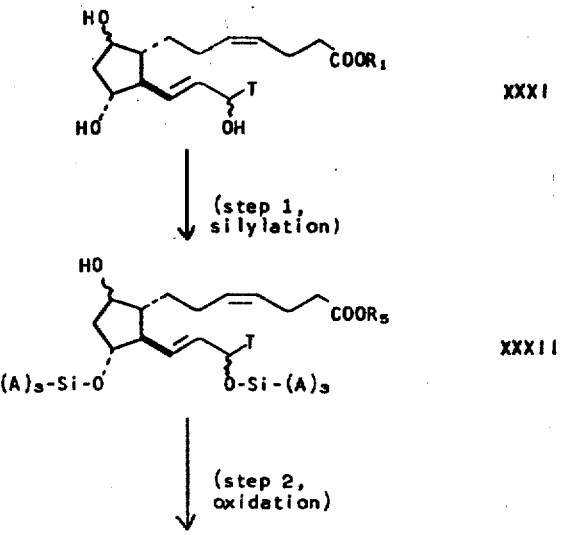

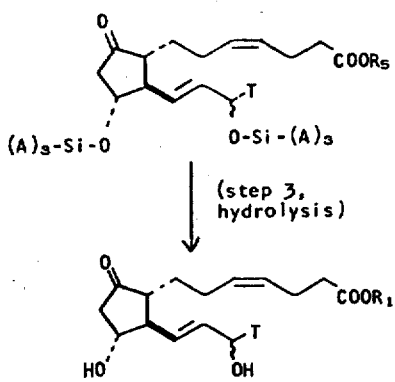

XXXIII

↓ (step 3, hydrolysis)

XXXIV

Consider, then, step 1 of Chart B, wherein the formula-XXXI compounds are selectively silylated at the C-11 and C-15 positions, by choice of reagents and conditions. Silylating agents are known in the art. See, for example, Pierce, "Silylation of Organic Compounds," Pierce Chemical Co., Rockford, Ill. (1968). Silylating agents of the type $(A)_3SiN(E)_2$, i.e. substituted silylamines wherein A is as defined above and E has the same definition as A, being the same or different, are useful for the above purpose at temperatures below about −25° C. A preferred temperature range is about −35° to −50°. At higher temperatures some silylation of C-9 hydroxyl groups as well as the C-11 and C-15 hydroxyl groups occurs, whereas at lower temperatures the rate of silylation is undesirably slow. Examples of the silylamine type silylating agents suitable for forming the formula-XXXII intermediates include pentamethylsilylamine, pentaethylsilylamine, N-trimethyl-silyldiethylamine, 1,1,1-triethyl-N,N-dimethylsilylamine, N,N-diisopropyl-1,1,1-tri-methylsilylamine, 1,1,1-tributyl-N,N-dimethylsilylamine, N,N-dibutyl-1,1,1-trimethylsilylamine, 1-isobutyl-N,N,1,1-tetramethylsilylamine, N-benzyl-N-ethyl-1,1,1-trimethyl-silylamine, N,N,1,1-tetramethyl-1-phenylsilylamine, N,N-diethyl-1,1-dimethyl-1-phenylsilylamine, N,N-diethyl-1-methyl-1,1-diphenylsilylamine, N,N-dibutyl-1,1,1-triphenyl-silylamine, and 1-methyl-N,N,1,1-tetraphenylsilylamine.

The reaction is carried out with exclusion of atmospheric moisture, for example under a nitrogen atmosphere. It is conveniently done in a solvent such as acetone or dichloromethane, although the silylating agent itself, when used in excess, may also serve as a liquid medium for the reaction. The reaction ordinarily is completed in a few hours, and should be terminated when the C-11 and C-15 hydroxyl groups are silylated, to avoid side reactions. The progress of the reaction is conveniently monitored by thinlayer chromatography (TLC), utilizing methods known in the art.

An excess of the reagent over that stoichiometrically required is used, preferably at least a four-fold excess. When $R_1$ in the formula-XXXI starting material is hydrogen, the —COOH moiety thereby defined may be partially or even completely transformed to —COO-Si-$(A)_3$, additional silylating agent being used for this purpose. Whether or not this occurs is immaterial for the success of the process, since —COOH groups are not changed by the subsequent steps and —COO-Si-$(A)_3$ groups are easily hydrolyzed to —COOH groups.

Consider, next, step 2 of Chart B, wherein the formula-XXXII 11,15-disilyl ether intermediate is oxidized to compound XXXIII. Oxidation reagents useful for this transformation are known in the art. An especially useful reagent for this purpose is the Collins reagent, i.e. chromium trioxide in pyridine. See J.C. Collins et al., Tetrahedron Lett., 3363 (1968). Dichloromethane is a suitable diluent for this purpose. A slight excess of the oxidant beyond the amount necessary to oxidize the C-9 secondary hydroxy group of the formula-XXXII intermediate is used. Reaction temperatures of below 20° C. should be used. Preferred reaction temperatures are in the range −10° to +10° C. The oxidation proceeds rapidly and is usually complete in about 5 to 20 minutes.

Finally in step 3 of Chart B, all silyl groups of the formula-XXXIII intermediates are removed by hydrolysis, thereby forming the formula-XXXIV PGE-type products. These hydrolyses are carried out by prior art procedures known to be useful for transforming silyl ethers and silyl esters to alcohols and carboxylic acids, respectively. See, for example, Pierce, cited above, especially p. 447 thereof. A mixture of water and sufficient of a water-miscible organic diluent to give a homogeneous hydrolysis reaction mixture represents a suitable reaction medium. Addition of a catalytic amount of an organic or inorganic acid hastens the hydrolysis. The length of time required for the hydrolysis is determined in part by the hydrolysis temperature. With a mixture of water and methanol at 25° C., several hours is usually sufficient for hydrolysis. At 0° C., several days is usually necessary. The formula-XXXIV PGE-type product is isolated by conventional means.

Those PGF-type compounds of formulas IX, XII, XVII, and XXI wherein $R_2$ is methyl or ethyl are transformed to the corresponding PGE-type compounds by the steps shown in Chart C. Therein, formula XLIV is generic to those PGF-type compounds named above. In Chart C, the symbols A, $R_1$, $R_5$, and ~ have the same meaning as in Chart B. M' represents either

or

wherein $R_3$ is methyl or ethyl. Following steps 1–3, which utilize essentially the same reagents and conditions as in steps 1–3 of Chart B, there are obtained the PGE-type compounds represented by formula XLVII. Under these conditions, the intermediates of formula XLV and XLVI are 11-silyl derivatives rather than the 11,15-disilyl derivatives of Chart B.

The novel 15-substituted PGF-type acids and esters of

CHART C

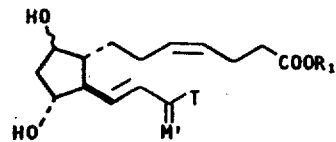

XLIV

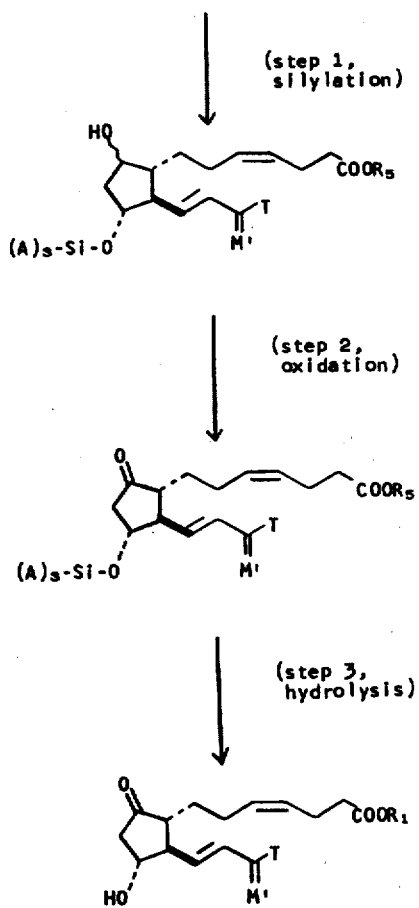

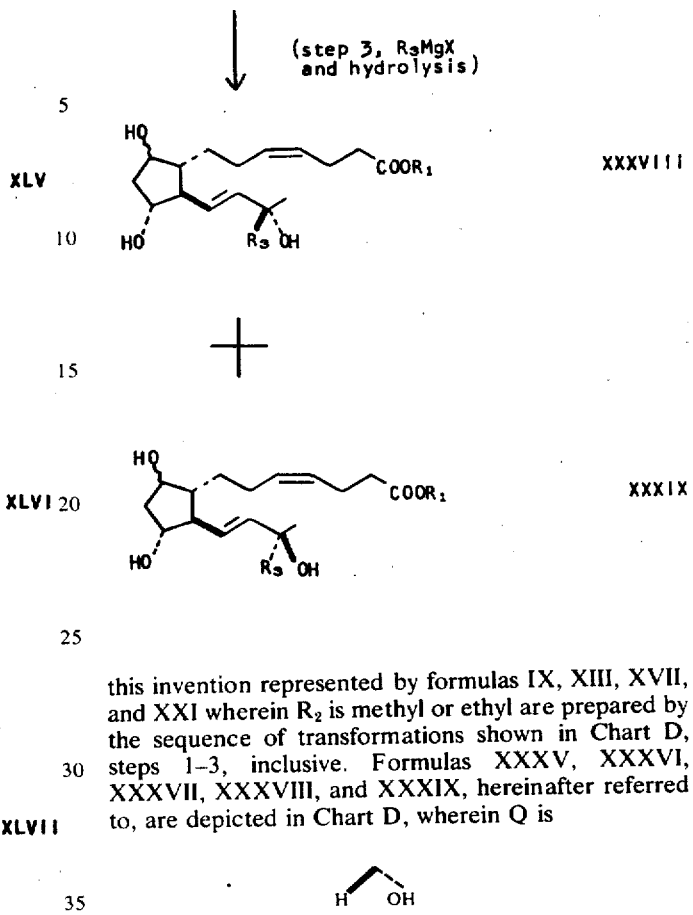

CHART D

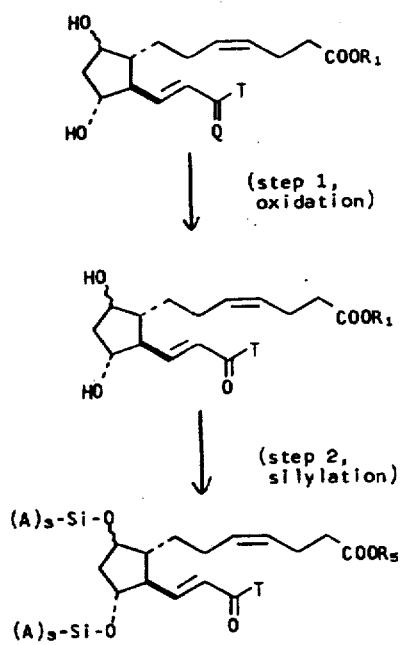

this invention represented by formulas IX, XIII, XVII, and XXI wherein $R_2$ is methyl or ethyl are prepared by the sequence of transformations shown in Chart D, steps 1–3, inclusive. Formulas XXXV, XXXVI, XXXVII, XXXVIII, and XXXIX, hereinafter referred to, are depicted in Chart D, wherein Q is

or

$R_3$ is methyl or ethyl, and A, $R_1$, $R_5$, T, and ~ are as defined for Chart B.

Consider, then, step 1 of Chart D, wherein the formula-XXXV PGF-type compounds are oxidized to the intermediate formula-XXXVI 15-oxo acids and esters. For this purpose, reagents such as 2,3-dichloro-5,6-dicyano-1,4-benzoquinone, activated manganese dioxide, or nickel peroxide are used, according to procedures known in the art. See Fieser et al., "Reagents for Organic Synthesis," John Wiley and Sons, Inc., New York, N.Y., (1967) pp. 215, 637, and 731.

Considering step 2 of Chart D, the formula-XXXVI 15-oxo compounds are transformed to silyl derivatives of formula XXXVII by procedures known in the art. See, for example, Pierce, "Silylation of Organic Compounds," Pierce Chemical Co., Rockford, Ill. (1968). Both hydroxy groups of the formula-XXXVI reactants are thereby transformed to —O-Si(A)$_3$ moieties wherein A is as defined above, and sufficient of the silylating agent is used for that purpose according to known procedures. When $R_1$ in the formula-XXXVI intermediate is hydrogen, the —COOH moiety thereby defined is simultaneously transformed to —COO-Si(A)$_3$, additional silylating agent being used for this purpose. This latter transformation is aided by excess silylating agent and prolonged treatment. When $R_1$ in formula XXXVI is alkyl, then $R_5$ in formula XXXVII will also be alkyl. The neccessary silylating agents for these transformations are known in the art or are prepared by methods known in the art. See, for example, Post, "Silicones and Other Organic Silicon Compounds," Reinhold Publishing Corp., New York, N.Y. (1949).

Considering step 3 of Chart D, the intermediate silyl compounds of formula XXXVII are transformed to the final 15-substituted compounds of Formulas XXXVIII and XXXIX by first reacting the silyl compound with a Grignard reagent of the formula $R_3MgHal$ wherein $R_3$ is as defined above, and Hal is chloro, bromo, or iodo. For this purpose, it is preferred that Hal be bromo. This reaction is carried out by the usual procedure for Grignard reactions, using diethyl ether as a reaction solvent and saturated aqueous ammonium chloride solution to hydrolyze the Grignard complex. The resulting disilyl, trisilyl, or tetrasilyl tertiary alcohol is then hydrolyzed with water to remove the silyl groups. For this purpose, it is advantageous to use a mixture of water and sufficient of a water-miscible solvent, e.g., ethanol to give a homogenous reaction mixture. The hydrolsis is usually complete in 2 to 6 hours at 25° C., and is preferably carried out in an atmosphere of an inert gas, e.g., nitrogen or argon.

The mixture of 15-α and 15-β isomers obtained by this Grignard reaction and hydrolysis is separated by procedures known in the art for separating mixtures of prostanoic acid derivatives, for example, by chromatography on neutral silica gel. In some instances, the lower alkyl esters, especially the methyl esters of a pair of 15-α and 15-β isomers are more readily separated by silica gel chromatography than are the corresponding acids. In those cases, it is advantageous to esterify the mixture of acids as described below, separate the two esters, and then, if desired, saponify the esters by procedures known in the art for saponification of prostaglandins F.

The 15-substituted PGE-type compounds represented by formulas VIII, XII, XVI, and XX are prepared from the above 15-substituted PGF-type compounds following the steps of Chart C, discussed above.

Chart E shows transformations from the formula XL PGE-type compounds to the corresponding PGF-, PGA-, and PGB-type compounds. In figures XL, XLI, XLII, and XLIII of Chart E, M is

or

wherein $R_2$ is hydrogen, methyl, or ethyl; and $R_1$, T, and ~ are as defined above for Chart B.

Thus, the various PGFβ-type compounds encompassed by formulas IX, XIII, XVII, and XXI, wherein ~ is beta, are prepared by carbonyl reductions of the corresponding PGE type compounds, e.g. formulas VIII, XII, XVI, and XX. For example, carbonyl reduction of 4,5-cis-didehydro-PGE$_1$ gives a mixture of 4,5-cis-didehydro-PGF$_{1\alpha}$ and 4,5-cis-didehydro-PGF$_{1\beta}$.

These ring carbonyl reductions are carried out by methods known in the art for ring carbonyl reductions of known prostanoic acid derivatives. See, for example, Bergstrom et al., Arkiv Kemi 19, 563 (1963), Acta. Chem. Scand. 16, 969 (1962), and British Specification No. 1,097,533. Any reducing agent is used which does not react with carbon-carbon double bonds or ester groups. Preferred reagents are lithium(tri-tert-butyoxy)aluminum hydride, the metal borohydrides, especially sodium, potassium and zinc

CHART E

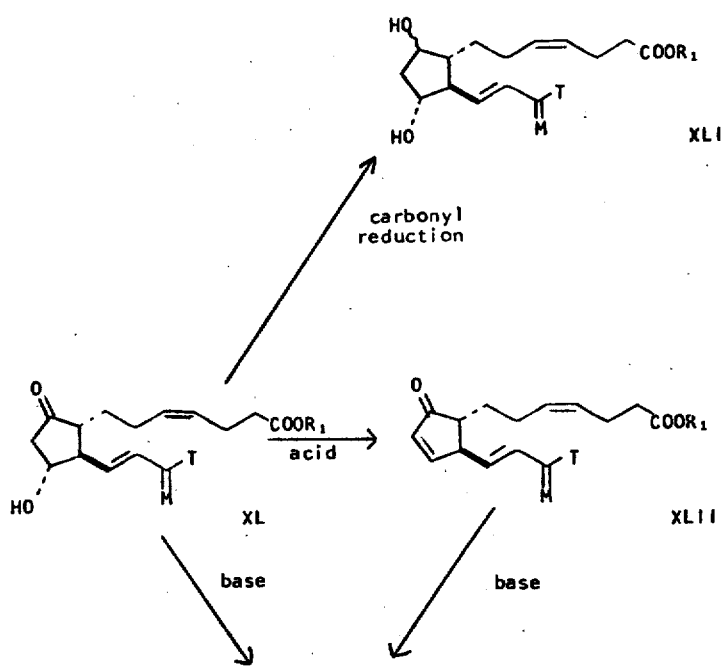

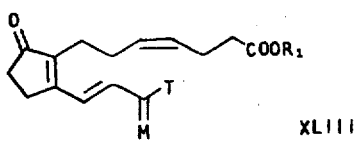

XLIII borohydrides, the metal trialkoxy borohydrides, e.g., sodium trimethoxyborohydride. The mixtures of alpha and beta hydroxy reduction products are separated into the individual alpha and beta isomers by methods known in the art for the separation of analogous pairs of known isomeric prostanoic acid derivatives. See, for example, Bergstrom et al., cited above, Granstrom et at., J. Biol. Chem. 240, 457 (1965), and Green et al., J. Lipid Research 5, 117 (1964). Especially preferred as separation methods are partition chromatographic procedures, both normal and reversed phase, preparative thin layer chromatography, and countercurrent distribution procedures.

The various PGA-type compounds encompassed by formulas X, XIV, XVIII, and XXII are prepared by acidic dehydration of the corresponding PGE-type compounds, e.g. formulas VII, XII, XVI, and XX. For example, acidic dehydration of 4,5-cis-didehydro-PGE$_1$ gives 4,5-cis-didehydro-PGA$_1$.

These acidic dehydrations are carried out by methods known in the art for acidic dehydrations of known prostanoic acid derivatives. See, for example, Pike et al., Proc. Nobel Symposium II, Stockholm (1966), Interscience Publishers, New York, pp. 162–163 (1967); and British Specification 1,097,533. Alkanoic acids of 2 to 6 carbon atoms, inclusive, especially acetic acid, are preferred acids for this acidic dehydration. Dilute aqueous solutions of mineral acids, e.g., hydrochloric acid, especially in the presence of a solubilizing diluent, e.g., tetrahydrofuran, are also useful as reagents for this acidic dehydration, although these reagents may cause partial hydrolysis of an ester reactant.

The various PGB-type compounds encompassed by formulas XI, XV, XIX, and XXIII are prepared by basic dehydration of the corresponding PGE-type compounds encompassed by formulas VIII, XII, XVI, and XX, or by ccontacting the corresponding PGA-type compounds encompassed by formulas X, XIV, XVIII, and XXII with base. For example, both 4,5,-cis-didehydro-PGE$_1$ and 4,5-cis-didehydro-PGA$_1$ give 4,5-cis-didehydro-PGB$_1$ on treatment with base. These basic dehydrations and double bond migrations are carried out by methods known in the art for similar reactions of known prostanoic acid derivatives. See, for example, Bergstrom et al., J. Biol. Chem. 238, 3555 (1963). The base is any whose aqueous solution has pH greater than 10. Preferred bases are the alkali metal hydroxides. A mixture of water and sufficient of a water-miscible alkanol to give a homogeneous reaction mixture is a suitable as a reaction medium. The PGE-type or PGA-type compound is maintained in such a reaction medium until no further PGBtype compound is formed, as shown by the characteristic ultraviolet light absorption near 278 m$\mu$ for the PGB-type compound.

Optically active products are obtained from optically active intermediates according to the process steps of Chart A. Likewise, optically active products are obtained by the transformations of optically active compounds following the processes of Charts B, C, D, and E. When racemic intermediates are used, and racemic products are obtained, these racemic products may be used in their racemic form or, if preferred, they may be resolved as optically active isomers by procedures known in the art.

For example, when final compound VIII to XXIII is a free acid, the dl form thereof is resolved into the d and l forms by reacting said free acid by known general procedures with an optically active base, e.g., brucine or strychnine, to give a mixture of two diastereooisomers which are separated by known general procedures, e.g., fractional crystallization, to give the separate diastereoisomeric salts. The optically active acid of formula VIII to XXIII is then obtained by treatment of the salt with an acid by known general procedures.

As discussed above, the stereochemistry at C-15 is not altered by the transformations of Chart A; the 15$\beta$ epimeric products of formula XXX are obtained from 15$\beta$ formula-XXVII reactants. Another method of preparing the 15$\beta$ products is by isomerization of the PGF$_1$- or PGE$_1$-type compounds having 15-(S) configuration, by methods known in the art. See, for example, Pike et al., J. Org. Chem. 34, 3552 (1969).

As discussed above, the processes of Charts A, B, C, D, and E lead variously to acids (R$_1$ is hydrogen) or to esters (R$_1$ is alkyl, cycloalkyl, aralkyl, phenyl or substituted phenyl, as defined above). When an acid has been prepared and an alkyl ester is desired, esterification is advantageously accomplished by interaction of the acid with the appropriate diazohydrocarbon. For example, when diazomethane is used, the methyl esters are produced. Similar use of diazoethane, diazobutane, and 1-diazo-2-ethylhexane, and diazodecane, for example, gives the ethyl, butyl, and 2-ethylhexyl and decyl esters, respectively.

Esterification with diaxohydrocarbons is carried out by mixing a solution of the diazohydrocarbon in a suitable inert solvent, preferably diethyl ether, with the acid reactant, advantageously in the same or a different inert diluent. After the esterification reaction is complete, the solvent is removed by evaporation, and the ester purified if desired by conventional methods, preferably by chromatography. It is preferred that contact of the acid reactants with the diazohydrocarbon be no longer than necessary to effect the desired esterification, preferably about one to about ten minutes, to avoid undesired molecular changes. Diazohydrocarbons are known in the art or can be prepared by methods known in the art. See for example, Organic Reactions, John Wiley and Sons, Inc., New York, N.Y., Vol. 8, pp. 389–394 (1954).

An alternative method for esterification of the carboxyl moiety of the acid compounds comprises transformation of the free acid to the corresponding silver salt, followed by interaction of that salt with an alkyl iodide. Examples of suitable iodides are methyl iodide, ethyl iodide, butyl iodide, isobutyl iodide, tert-butyl iodide, and the like. The silver salts are prepared by conventional methods, for example, by dissolving the acid in cold dilute aqueous ammonia, evaporating the excess ammonia at reduced pressure, and then adding the stoichiometric amount of silver nitrate.

The final formula VIII-to-XXIII compounds prepared by the processes of this invention, in free acid form, are transformed to pharmacologically acceptable salts by neutralization with appropriate amounts of the corresponding inorganic or organic base, examples of which correspond to the cations and amines listed above. These transformations are carried out by a variety of procedures known in the art to be generally useful for the preparation of inorganic, i.e., metal or ammonium, salts, amine acid addition salts, and quaternary ammonium salts. The choice of procedure depends in part upon the solubility characteristics of the particular salt to be prepared. In the case of the inorganic salts, it is usually suitable to dissolve the formula VIII-to-XXIII acid in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-miscible solvent of moderate polarity, for example, a lower alkanol or a lower alkanone, gives the solid inorganic salt if that form is desired.

To produce an amine salt, the formula VIII-to-XXIII acid is dissolved in a suitable solvent of either moderate or low polarity. Examples of the former are ethanol, acetone, and ethyl acetate. Examples of the latter are diethyl ether and benzene. At least a stoichiometric amount of the amine corresponding to the desired cation is then added to that solution. If the resulting salt does not precipitate, it is usually obtained in solid form by addition of a miscible diluent of low polarity or by evaporation. If the amine is relatively volatile, any excess can easily be removed by evaporation. It is preferred to use stoichiometric amounts of the less volatile amines.

Salts wherein the cation is quaternary ammonium are produced by mixing the formula VIII-to-XXIII acid with the stoichiometric amount of the corresponding quaternary ammonium hydroxide in water solution, followed by evaporation of the water.

The final formula VIII-to-XXIII acids or esters prepared by the processes of this invention are transformed to lower alkanoates by interaction of the formula VIII-to-XXIII hydroxy compound with a carboxyacylating agent, preferably the anhydride of a lower alkanoic acid, i.e., an alkanoic acid of two to 8 carbon atoms, inclusive. For example, use of acetic anhydride gives the corresponding acetate. Similar use of propionic anhydride, isobutyric anhydride, and hexanoic acid anhydride gives the corresponding carboxyacylates.

The carboxyacylation is advantageously carried out by mixing the hydroxy compound and the acid anhydride, preferably in the presence of a tertiary amine such as pyridine or triethylamine. A substantial excess of the anhydride is used, preferably about 10 to about 10,000 moles of anhydride per mole of the hydroxy compound reactant. The excess anhydride serves as a reaction diluent and solvent. An inert organic diluent, for example, dioxane, can also be added. It is preferred to use enough of the tertiary amine to neutralize the carboxylic acid produced by the reaction, as well as any free carboxyl groups present in the hydroxy compound reactant.

The carboxyacylation reaction is preferably carried out in the range about 0° to about 100° C. The necessary reaction time will depend on such factors as the reaction temperature, and the nature of the anhydride and tertiary amine reactants. With acetic anhydride, pyridine, and a 25° C. reaction temperature, a 12 to 24-hour reaction time is used.

The carboxyacylated product is isolated from the reaction mixture by conventional methods. For example, the excess anhydride is decomposed with water, and the resulting mixture acidified and then extracted with a solvent such as diethyl ether. The desired carboxyacylate is recovered from the diethyl ether extract by evaporation. The carboxyacylate is then purified by conventional methods, advantageously by chromatography.

By this procedure, the formula VIII, XII, XVI, and XX PGE-type compounds are transformed to dialkanoates, the formula IX, XIII, XVII, and XXI PGF-type compounds are transformed to trialkanoates, and the formula X, XIV, XVIII, and XXII PGA-type and formula XI, XV, XIX, and XXIII PGB-type compounds are transformed to monalkanoates.

When a PGE-type dialkanoate is transformed to a PGF-type compound by carbonyl reduction as shown in Chart E, a PGF-type dialkanoate is formed and is used for the above-described purposes as such or is transformed to a trialkanoate by the above-described procedure. In the latter case, the third alkanoyloxy group can be the same as or different from the two alkanoyloxy groups present before the carbonyl reduction.

DESCRIPTION OF THE PREFERRED EMBODIMENTS

The invention can be more fully understood by the following examples.

All temperatures are in degrees centigrade.

Infrared absorption spectra are recorded on a Perkin-Elmer model 421 infrared spectrophotometer. Except when specified otherwise, undiluted (neat) samples are used.

Mass spectra are recorded on an Atlas CH-4 mass spectrometer with a TO-4 source (ionization voltage 70 ev).

"Brine", herein, refers to an aqueous saturated sodium chloride solution.

EXAMPLE 1

3α,5α-Dihydroxy-2β-(3α-hydroxy-trans-1-octenyl)-1α-cyclopentanepropionaldehyde δ Lactol (Formula XXIX: T is 1-pentyl and ~ is alpha).

Refer to Chart A. A suspension of methoxymethyltriphenylphosphonium chloride (Levine, J. Am. Chem. Soc. 80, 6150 (1958), 32.4 g.) in 150 ml. of tetrahydrofuran (THF) is cooled to −15° C. and to it is added 69.4 ml. of butyllithium (1.6 M. in hexane) in 45 ml. of THF. After 30 min. there is added a solution of the formula-XXVII 3α,5α-dihydroxy-2β-(3α-hydroxy-trans-1-octenyl)-1α-cyclopentaneacetaldehyde γ lactol bis(tetrahydropyranyl) ether (Corey et al., J. Am. Chem. Soc. 92, 397 (1970), 10.0 g.) in 90 ml. of THF. The mixture is stirred for 1.5 hrs., meanwhile warming to about 25° C., and is then concentrated under reduced pressure. The residue is partitioned between dichloromethane and water, and the organic phase is dried and concentrated. This residue is then subjected to chromatography over silica gel, eluting with cyclopexaneethyl acetate (2:1). Those fractions shown by thin-layer chromatography (TLC) to contain the formula-XXVIII intermediate are combined and concentrated to yield that enol-ether, 5.2 g.

The above enol-ether, in 20 ml. of THF, is hydrolyzed with 50 ml. of 66% acetic acid at about 57° G. for 2.5 hrs. The mixture is concentrated under reduced pressure. Toluene is added to the residue and the solution is again concentrated. Finally the residue is subjected to chromatography on silica gel, eluting with chloroform-methanol (6:1). The title compound is obtained by combining and concentrating suitable fractions, 2.54 g.; recrystallized from ethyl acetate, m.p. 121°–123° C., infrared absorption at 3500, 1315, 1220, 1140, 1120, 1045, 1020, and 970 cm$^{-1}$.

Following the procedures of Example 1, but replacing the formula-XXVII compound with the corresponding racemic 3α,5α-dihydroxy-2β-(3α-hydroxy-trans-1-octenyl)-1α-cyclopentaneacetaldehyde γ lactol bis(tetrahydropyranyl) ether (Corey et al., J. Am. Chem. Soc. 91, 5675 (1969)), there is obtained the corresponding racemic δ lactol, namely, dl-3α,5α-dihydroxy-2β-(3α-hydroxy-trans-1-octenyl)-1α-cyclopentanepropionaldehyde δ lactol.

Following the procedures of Example 1, but replacing the formula-XXVII compound with the corresponding 3β-hydroxy ether compound, there is obtained the corresponding formula-XXIX 3β-hydroxy compound, namely 3α,5α-dihydroxy-2β-(3β-hydroxy-trans-1-octenyl)-1α-cyclopentanepropionaldehyde δ lactol.

Likewise following the procedures of Example 1, but replacing the formula-XXVII compound with the corresponding racemic 3β-hydroxy ether compound, there is obtained the corresponding racemic 3β-hydroxy δ lactol, namely dl-3α,5α-dihydroxy-2β-(3β-hydroxy-trans-1-octenyl)-1α-cyclopentanepropionaldehyde δ lactol.

EXAMPLE 2

4,5-cis-Didehydro-PGF$_{1α}$ (Formula IX: R$_1$ and R$_2$ are hydrogen, and ~ is alpha).

Refer to Chart A. 3-Carboxypropyltriphenylphosphonium bromide is prepared by heating triphenylphosphine (156.8 g.) and 4-bromobutyric acid (100 g.) in 125 ml. of benzene at reflux for 18 hrs. The crystalline product is filtered off, washed with benzene, and recrystallzed from ethanolacetonitrile-ether, 150 g., m.p. 247°–249° C.

The above phosphonium bromide (10.6 g.) is added to sodio methylsulfinylcarbanide prepared from sodium hydride (2.08 g., 57%) and 30 ml. of dimethyl sulfoxide, and the resulting Wittig reagent is combined with the Formula-XXIX lactol (Example 1, 1.76 g.) in 20 ml. of dimethyl sulfoxide. The mixture is stirred overnight, diluted with about 200 ml. of benzene, and washed with potassium hydrogen sulfate solution. The two lower layers are washed with dichloromethane, and the organic phases are combined, washed with brine, dried, and concentrated under reduced pressure. The residue is subjected to chromatography over acid-washed silica gel, eluting with ethyl acetate-isomeric hexanes (3:1). Those fractions shown to contain the desired compound by TLC are combined and concentrated to yield the title compound, 0.14 g.; high resolution mass spectral peak (trimethylsilyl derivative) at 642.3929.

Following the procedures of Example 2, but replacing the formula-XXIX lactol with either the corresponding racemic lactol, the corresponding formula-XXIX 3β-hydroxy lactol, or the corresponding racemic 3β-hydroxy lactol obtained following Example 1, there is obtained the corresponding dl-4,5-cis-didehydro-PGF$_{1α}$, the formula-XVII 4,5-cis-didehydro-15β-PGF$_{1α}$ product, or dl-4,5-cis-didehydro-15β-PGF$_{1α}$.

EXAMPLE 3

4,5-cis-Didehydro-PGF$_{1α}$, Methyl Ester (Formula IX: R$_1$ is methyl, R$_2$ is hydrogen, and ~ is alpha).

A solution of diazomethane (about 50% excess) in diethyl ether (25 ml.) is added to a solution of 4,5-cis-didehydro-PGF$_{1α}$ (Example 2, 50 mg.) in 25 ml. of a mixture of methanol and diethyl ether (1:1). The mixture is left standing at 25° C. for 5 min. and then is concentrated under reduced pressure to the title compound.

Likewise following the procedures of Example 3, the methyl esters of dl-4,5-cis-didehydro-PGF$_{1α}$, 4,5-cis-didehydro-15β-PGF$_{1α}$, and dl-4,5-cis-didehydro-15β-PGF$_{1α}$ are prepared.

EXAMPLE 4

4,5-cis-Didehydro-PGE$_1$, Methyl Ester (Formula XXXIV: P$_1$ is methyl, T is 1-pentyl, and ~ is alpha).

Refer to Chart B. 1. A solution of 4,5-cis-didehydro-PGF$_{1α}$, methyl ester (Example 3, 480 mg.) in 20 ml. of acetone is cooled to about −50° C. and to it is added 4 ml. of N-trimethylsilyldiethylamine. The mixture is kept under nitrogen at −50° C. for 2.5 hrs. Progress of the reaction is monitored by TLC. The reaction mixture is diluted with about 200 ml. of diethyl ether. The solution is washed with about 150 ml. of cold brine and cold saturated potassium bicarbonate solutions. The ether extract is concentrated to a residue containing 4,5-cis-didehydro-PGF$_{1α}$, 11,15-bis-(trimethylsilyl) ether, methyl ester (Formula XXXII).

2. For the oxidation step, a solution of the above 11,15-bis(trimethylsilyl) ether in dichloromethane (4 ml.) is added to a solution of CrO$_3$-pyridine (prepared from 0.26 g. of CrO$_3$ and 0.4 ml. of pyridine in 16 ml. of dichloromethane). The mixture is stirred for 5 min. at about 0° C. and 5 min. at about 25° C., then diluted with 10 ml. of ethyl acetate and filtered through silica gel. The solution, together with rinsings, is concentrated under reduced pressure.

3. The product of step 2 is hydrolyzed in 6 ml. of methanol, 1 ml. of water, and about 0.1 ml. of acetic acid at about 35° C. for 15 min. The volatiles are removed under reduced pressure and the residue is partitioned between dichloromethane and water. The organic phase is separated, dried over sodium sulfate, and concentrated under reduced pressure. The residue is chromatographed on silica gel, eluting with ethyl acetate-SKellysolve B (isomeric hexanes) (4:1). Those factions containing the title compound free of starting material and impurities are combined and concentrated to yield the title compound, 77 mg.; mass spectral peaks (for trimethylsilylated derivative) at 495, 492, 479, 439, 420 and 349; mass 510.3198.

Following the procedures of Example 4, but replacing 4,5-cis-didehydro-PGF$_{1α}$, methyl ester with dl-4,5-cis-didehydro-PGF$_{1α}$, methyl ester obtained following Example 3, there is obtained dl-4,5-cis-didehydro-PGE$_1$, methyl ester.

Following the procedures of Example 4, but replacing 4,5-cis-didehydro-PGF$_{1α}$, methyl ester, with 4,5-cis-didehydro-15β-PGF$_{1α}$ obtained following Example 2, there is obtained the formula-XVI 4,5-cis-didehydro-15β-PGE$_1$ product.

Likewise, using dl-4,5-cis-didehydro-15β-PGF$_{1α}$, methyl ester, there is obtained dl-4,5-cis-didehydro-15β-PGE$_1$, methyl ester.

EXAMPLE 5

4,5-cis-Didehydro-PGF$_{1\beta}$, Methyl Ester (Formula IX: R$_1$ is methyl, R$_2$ is hydrogen, and ~ is beta).

Refer to Chart E. A solution of sodium borohydride (300 mg.) in 6 ml. of ice-cold methanol is added to a solution of 4,5-cis-didehydro-PGE$_1$, methyl ester (Example 4, 650 mg.) in 30 ml. of methanol at −5° C. The mixture is stirred for 0.5 hrs. at 0° C. and 5 ml. of acetone is added, after which the mixture is stirred for 5 min. and made slightly acid with acetic acid. The mixture is evaporated under reduced pressure until most of the methanol and acetone are removed, then the residue is extracted with dichloromethane. The extract is washed with water, dilute aqueous sodium bicarbonate, and brine, then dried over sodium sulfate and evaporated under reduced pressure to give a residue. This residue is chromatographed over silica gel wet-packed in ethyl acetate, eluting with 2%, 4%, 7.5%, and 10% ethanol in ethyl acetate, taking 25 ml. fractions. Those fractions containing the title compound free of starting material and impurities, as shown by TLC, are combined and concentrated to yield the formula-IX product.

Following the procedure of Example 5, the corresponding 15$\beta$ compound and the respective racemic compounds are each reduced and separated as the corresponding 4,5-cis-didehydro-PGF$_{1\beta}$ -type compounds.

EXAMPLE 6

4,5-cis-17,18-cis-Tetradehydro-PGF$_{1\alpha}$ (Formula XIII: R$_1$ and R$_2$ are hydrogen, and ~ is alpha).

Following the procedures of Example 1 and 2, but replacing the formula-XXVII 3$\alpha$,5$\alpha$-dihydroxy-2$\beta$-(3$\alpha$-hydroxy-trans-1-octenyl)-1$\alpha$-cyclopentaneacetaldehyde $\gamma$ lactol bis(tetrahydropyranyl) ether of Example 1 with 3$\alpha$,5$\alpha$-dihydroxy-2$\beta$-(3$\alpha$-hydroxy-trans-1-cis-17-octadienyl)1$\alpha$-cyclopentaneacetaldehyde $\gamma$ lactol bis(tetrahydropyranyl) ether (Corey et al., J. Am. Chem. Soc. 93, 1490 (1971)), there is obtained first the corresponding formula-XXVIII intermediate enol-ether, then the formula-XXIX lactol, wherein T is cis 1-pent-2-enyl, and finally the title compound.

Following the procedures of example 6 but replacing the formula-XXVII ether of that example with the corresponding 3$\beta$-hydroxy ether, namely, 3$\alpha$,5$\alpha$-dihydroxy-2$\beta$-(3$\beta$-hydroxy-trans-1-cis-5-octadienyl)-1$\alpha$-cyclopentaneacetaldehyde $\gamma$ lactol bis(tetrahydropyranyl) ether, there is obtained the corresponding formula-XXI 4,5-cis-17,18-cis-tetrahydro-15$\beta$-PGF$_{1\alpha}$ product.

Following the procedures of Example 6 but using the appropriate racemic intermediate, there is obtained dl-4,5-cis-17,18-cis-tetradehydro-PGF$_{1\alpha}$ and dl-4,5-cis-17,18-cis-tetradehydro-15$\beta$-PGF$_{1\alpha}$.

EXAMPLE 7

4,5-cis-17,18-cis-Tetradehydro-PGE$_1$ (Formula XII: R$_1$ and R$_2$ are hydrogen).

Following the procedures of Example 4, but replacing the 4,5-cis-didehydro-PGF$_{1\alpha}$, methyl ester of that Example with formula-XIII 4,5-cis-17,18-cis-tetradehydro-PGF$_{1\alpha}$ (Example 5), there is obtained the title compound.

Likewise following the procedures of Example 7, but using formula-XXI 4,5-cis-17,18-cis-tetradehydro-15$\beta$-PGF$_{1\alpha}$, there is obtained the corresponding formula-XX 4,5-cis-17,18-cis tetradehydro-15$\beta$-PGE$_1$ compound.

Following the procedures of Example 7, but using the racemic tetradehydro PGF$_{1\alpha}$ - and 15$\beta$-PGF$_{1\alpha}$ -type compounds, there is obtained dl-4,5-cis-17,18-cis-tetradehydro-PGE$_{1\alpha}$ and dl-4,5-cis-17,18-cis-tetradehydro-15$\beta$-PGE$_1$.

EXAMPLE 8

4,5-cis-Dihydro-PGA$_1$ (Formula X: R$_1$ and R$_2$ are hydrogen).

Refer to Chart E. A solution of 4,5-cis-didehydro-PGE$_1$ methyl ester (Example 4, 300 mg.), 4 ml. of tetrahydrofuran and 4 ml. of 0.5 N hydrochloric acid is left standing at 25° C. for 5 days. Brine and dichloromethane-ether (1:3) are added and the mixture is stirred. The organic layer is separated, dried and concentrated. The residue is dissolved in ether and the solution is extracted with saturated aqueous sodium bicarbonate. The aqueous phase is acidified with dilute hydrochloric acid and extracted with dichloromethane. This extract is dried and concentrated to yield the formula-X title compound.

Following the procedure of Example 8, the corresponding 4,5-cis-didehydro-15$\beta$-PGA$_1$ and racemic products are obtained.

EXAMPLE 9

4,5-cis-Didehydro-PGB$_1$ (Formula XI: R$_1$ and R$_2$ are hydrogen).

Refer to Chart E. A solution of 4,5-cis-didehydro-PGE$_1$ methyl ester (Example 4, 200 mg.) in 100 ml. of 50% aqueous ethanol containing about one gram of potassium hydroxide is kept at 25° C. for 10 hrs. under nitrogen. Then, the solution is cooled to 10° C. and neutralized by addition of 3 N. hydrochloric acid at 10° C. The resulting solution is extracted repeatedly with ethyl acetate, and the combined ethyl acetate extracts are washed with water and then with brine, dried, and concentrated to give the desired formula-XI title compound.

Following the procedure of Example 9, the corresponding 4,5-cis-didehydro-15$\beta$-PGB$_1$ and racemic products are obtained.

We claim:

1. An optically active compound of the formula

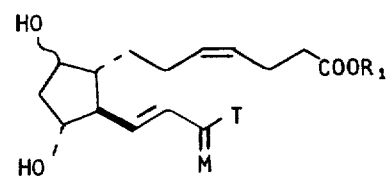

or a racemic compound of that formula and the mirror image thereof, wherein ~ indicates attachment of hydroxyl to the cyclopentane ring in alpha or beta configuration; wherein M is

or

wherein $R_2$ is hydrogen, methyl, or ethyl; wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive; and wherein T is 1-pentyl or cis 1-pent-2-enyl; including the lower alkanoates thereof, and the pharmacologically acceptable salts thereof when $R_1$ is hydrogen.

2. A compound according to claim 1 wherein T is cis 1-pent-2-enyl.

3. 4,5-cis-17,18-cis-Tetradehydro-PGF$_{1\alpha}$ , a compound according to claim 2 wherein ~ indicates attachment of hydroxyl in the alpha configuration, M is

and $R_1$ is hydrogen.

4. An optically active compound of the formula

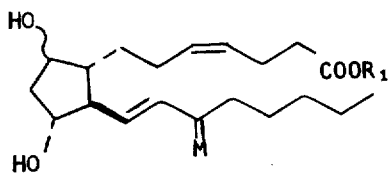

or a racemic compound of that formula and the mirror image thereof, wherein ~ indicates attachment of hydroxyl to the cyclopentane ring in alpha or beta configuration; wherein M is

or

wherein $R_2$ is hydrogen, methyl, or ethyl; and wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive; including the lower alkanoates thereof, and the pharmacologically acceptable salts thereof when $R_1$ is hydrogen.

5. 4,5-cis-Didehydro-PGF$_{1\alpha}$ , methyl ester, a compound according to claim 4.

6. 4,5-cis-Didehydro-PGF$_{1\beta}$ , a compound according to claim 4.

7. 4,5-cis-Didehydro-PGF$_{1\beta}$ , methyl ester, a compound according to claim 4.

8. 15(S)-15-Methyl-4,5-cis-didehydro-PGF$_{1\alpha}$ , a compound according to claim 4.

9. 15(S)-15-Methyl-4,5-cis-didehydro-PGF$_{1\alpha}$ , methyl ester, a compound according to claim 4.

10. 15(R)-15-Methyl-4,5-cis-didehydro-PGF$_{1\alpha}$ , a compound according to claim 4.

11. 15(R)-15-Methyl-4,5-cis-didehydro-PGF$_{1\alpha}$ , methyl ester, a compound according to claim 4.

12. 4,5-cis-Didehydro-PGF$_{1\alpha}$ , a compound according to claim 4 wherein ~ indicates attachment of hydroxyl in the alpha configuration, M is

and $R_1$ is hydrogen.

* * * * *

UNITED STATES PATENT OFFICE
CERTIFICATE OF CORRECTION

Patent No. 3,954,835      Dated 4 May 1976

Inventor(s) Bengt Samuelsson, Barney J. Magerlein

It is certified that error appears in the above-identified patent and that said Letters Patent are hereby corrected as shown below:

Column 2, line 65, "$PGE_2$, $PGF_2\alpha$" should read -- $PGE_2$, $PGE_3$, $PGF_2\alpha$ --.
Column 6, line 10, "cvulation" should read -- ovulation --.
Column 9, line 38, "in β (beta)" should read -- in R (beta) --.
Column 9, line 44, "$PGF_1$" should read -- $PGF_1\alpha$ --.
Column 10, line 3, "3-phenybutyl," should read -- 3-phenylbutyl, --.
Column 11, line 40, "$R_2$" should read -- $R_3$ --.
Column 11, line 46, "$R_2$" should read -- $R_3$ --.
Column 12, line 34, "strking" should read -- striking --.
Column 16, line 15, "PCF-type" should read -- PGF-type --.
Column 16, line 27, "wherein R is $R_1$" should read -- wherein $R_5$ is $R_1$ --.
Column 18, line 38, "formulas IX, XII," should read -- formulas IX, XIII --.
Column 23, line 25, "formulas VII, XII," should read -- formulas VIII, XI --.
Column 23, line 45, "ccontacting" should read -- contacting --.
Column 24, lines 9-10, "diastereooisomers" should read -- diastereoisomers --.
Column 26, line 59-60, "cyclopexaneethyl" should read -- cyclohexane-ethyl --.
Column 28, line 19, "$P_1$" should read -- $R_1$ --.

Column 30, line 10, "-$PGE_1\alpha$" should read -- -$PGE_1$ --.

Signed and Sealed

Eighteenth Day of Aug...

[SEAL]

Attest:

Attesting Officer

GERALD J. MOSSINGHOFF

Commissioner of Patents and Tradem...